United States Patent [19]

Hartert

[11] 4,202,204
[45] May 13, 1980

[54] APPARATUS AND METHOD FOR MEASURING CHANGES IN CONDITIONS IN COAGULATING LIQUIDS

[75] Inventor: Hellmut Hartert, Kaiserslautern, Fed. Rep. of Germany

[73] Assignee: Dr. E. Fresenius Chem.-Pharm. Industrie KG, Oberursel, Fed. Rep. of Germany

[21] Appl. No.: 941,587

[22] Filed: Sep. 12, 1978

[30] Foreign Application Priority Data

Sep. 13, 1977 [DE] Fed. Rep. of Germany ....... 2741060

[51] Int. Cl.² .................... G01N 11/10; G01N 33/16
[52] U.S. Cl. ........................................ 73/64.1; 73/59
[58] Field of Search ................... 73/59, 60, 54, 64.1

[56] References Cited

U.S. PATENT DOCUMENTS

| | | | |
|---|---|---|---|
| 3,714,815 | 2/1973 | Hartert | 73/64.1 |
| 3,722,262 | 3/1973 | Gilinson, Jr. et al. | 73/59 |
| 3,751,975 | 8/1973 | Katsura | 73/59 |
| 4,045,999 | 9/1977 | Palmer | 73/59 |
| 4,148,216 | 4/1979 | Do et al. | 73/59 |

FOREIGN PATENT DOCUMENTS

| | | | |
|---|---|---|---|
| 1558516 | 1/1969 | France | 73/64.1 |
| 602825 | 4/1978 | U.S.S.R. | 73/64.1 |

OTHER PUBLICATIONS

Kaulla et al., *Verh. Dt. Ges. inn. Med.*, pp. 1183–1188, 1977.

*Primary Examiner*—Gerald Goldberg
*Assistant Examiner*—Joseph W. Roskos
*Attorney, Agent, or Firm*—Toren, McGeady and Stanger

[57] ABSTRACT

The coagulation of blood is measured by introducing the blood into an annular gap in a beaker formed between the inner surface of the beaker and a cylindrical member depending into the beaker. The beaker is mounted on the upper end of a rod-like support. A coil arrangement about the lower part of the rod-like support impresses a circular orbiting motion on the support and beaker. Another core associated with the rod-like support measures changes in amplitude of the support produced by the development of fibrin in the blood sample in the annular gap.

11 Claims, 2 Drawing Figures

APPARATUS AND METHOD FOR MEASURING CHANGES IN CONDITIONS IN COAGULATING LIQUIDS

BACKGROUND OF THE INVENTION

In the U.S. Pat. No. 3,714,815 disclosed for performing continuous measurements of coagulating liquids, preferably blood and derivatives thereof. Which apparatus has means for producing shearing and deformation effects in the coagulating fluid in the form of a circularly cylindrical beaker and a test member which also has a circularly cylindrical configuration and is suspended from a torsion wire and is located in the beaker. An annular gap between the beaker and the test member receives the fluid being measured. An orbital motion is imparted by appropriate means to the wall surfaces of the beaker which confine the fluid.

This apparatus is designed and adjusted such that the peripheral speed of the orbital movement substantially approximates the rate of flow of the blood in human blood vessels. In this patent, it has already also been proposed, inter alia, to produce the orbital movement by a rotating electrical field which correspondingly acts upon the beaker.

Thus, it has been known to measure the coagulation of blood by subjecting the fibrin, produced during coagulation, to a specific shearing stress. By appropriate metering of this shearing stress, the resilient resistance of the coagulum can be increased far more rapidly compared with an apparatus in which the fluid is not subjected to a metered shearing stress of this kind during coagulation, that is, during the formation of the coagulum. Thus, it is far simpler to distinguish between normal and pathological blood coagula than with the original apparatus described in the above patent. This renders it possible to provide a substantial improvement in the diagnostic routine. At the same time, it is possible to afford a sharp definition of the so-called coagulation time which elapses until the coagulum commences to form and which is normally difficult to define.

SUMMARY OF THE INVENTION

Based on the fundamental ideas of the above patent, and in accordance with the invention, an improved apparatus is proposed as well as a preferred measuring method to be performed by this improved apparatus. The improved apparatus is distinguished essentially in that the beaker for receiving the fluid is arranged at the upper end of an upright resilient rod. Located around the lower end of the rod is a plurality of coils forming a rotating electro-magnetic field. Cores entering the coils are secured to and extend radially from the rod. The movement of the entire arrangement, produced by the various components of the measuring apparatus and the fluid to be measured, is picked up by a further, laterally disposed coil whose core is also arranged radially on the rod. The rod is clamped in a resilient diaphragm which extends radially from the rod and serves to hold the entire arrangement.

Furthermore, a vibration-damping element acting upon the rod may be provided.

In the first instance, the same measurements with the evaluation of the same changes in the fluid to be measured can be performed by this arrangement as are performed by the apparatus disclosed in the above-mentioned patent. However, in addition to this, the present arrangement can be adjusted in a simple manner to a specific natural oscillation frequency, this being of importance in connection with the method to be performed by the present apparatus.

With this method, the measured values are ascertained in the resonance range of the natural oscillation of the measuring arrangement. Unexpectedly, it has transpired that, with a method of this type, the values coming from the pick-up coil and which can be recorded by, for example, a curve tracer, exhibit distict maxima in dependence upon the states of change with are of interest in the fluid to be measured.

Furthermore, it was found that the most favourable natural frequency of the arrangement is approximately 35 Hz, and usable measurement results can also be obtained at approximately twice the frequency and half the frequency, only, of course, taking into account certain variations in wave length and wave amplitude which are dependent upon one another, i.e. the frequency and the amplitude.

Thus, the formation of the resilient fibrin coagulum can be detected with even greater sensitivity by the new appartatus in that the resilient resistance of the fibrin coagulum, increasing during coagulation, leads to the change of the natural frequency of the resiliently suspended measuring sensor, that is, the rod. This rod can be regarded as an orbitally oscillating pendulum. This change in the natural frequency leads to a shift relative to the forced drive frequency. According to the chosen starting position, there is a phase shift between the measuring sensor and the drive and also a change in amplitude in strict dependence, hitherto not attained, upon the quality and the quantity of the formation of the resilient material, such as the fibrin coagulum in the blood, which are thus rendered measurable.

The shearing stress exerted in a physiologically limited range on the coagulum produced, multiplies the resilient resistance of the fibrin network if the mechanical load resulting from the shearing stress acts during the production of the fibrin network. In other words, the fibrin network would be substantially more open in the final state if it were not built up under shearing load. Furthermore, the resonance shift caused by the object to the measured, that is the fibrin coagulum, is rendered usable for the measurement. Both of these factors lead to a considerable increase in, and thus easier recognition of, the differences between normal and pathological coagulation processes.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there is illustrated and described a preferred embodiment of the invention.

DETAILED DESCRIPTION OF THE INVENTION

Figure 1:
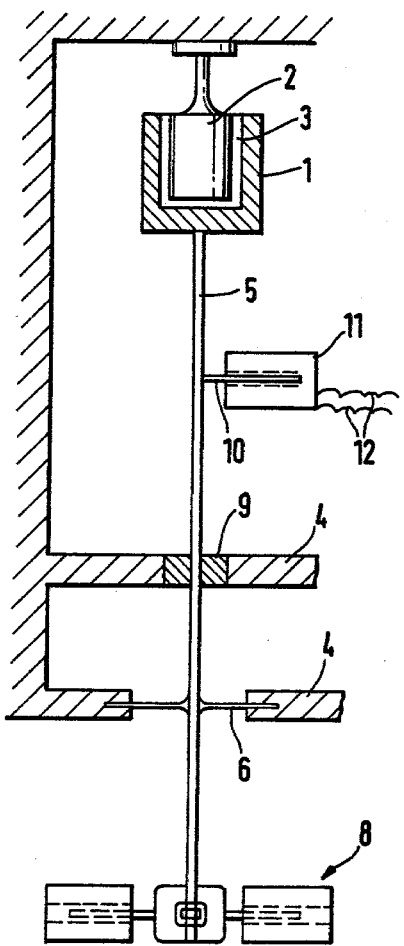
FIG. 1 is an elevational view partly in section of a measuring apparatus embodying the present invention.

FIG. 1 shows the parts which are important and critical to the action of the apparatus. A cylindrical member 2 is inserted in a known manner into a beaker 1 which is at the same time the actual testing member. The fluid, whose coagulation processes are to be measured, is introduced into the annular gap 3 formed between the two parts. In contrast to the rheosimulator, the cylindrical member 2 is rigidly connected to the frame 4 of the apparatus. The beaker 1 is arranged at the upper end of a rod 5 which is made from rigid material and which is mounted in the frame 4 of the apparatus by means of a circular resilient diaphragm 6. A coil arrangement 8 at the lower end of the rod 5 below the diaphragm 6 produces a rotating electro-magnet field and imparts to the rod 5 an orbital movement which differs in a specific manner from the natural frequency of the rod 5 and which is of, for example, somewhat higher frequency. The circular oscillation can be damped by means of a damping device 9. The damping device can comprise, for example, an annular member of resilient or non-resilient material which is mounted in the frame 4 and which embraces the rod 5.

A further core 10, which enters a pick-up coil 11, is arranged on and extends radially of the rod 5 and is connected by way of leads 12 to any optional indicating element such as a curve tracer.

Figure 2:
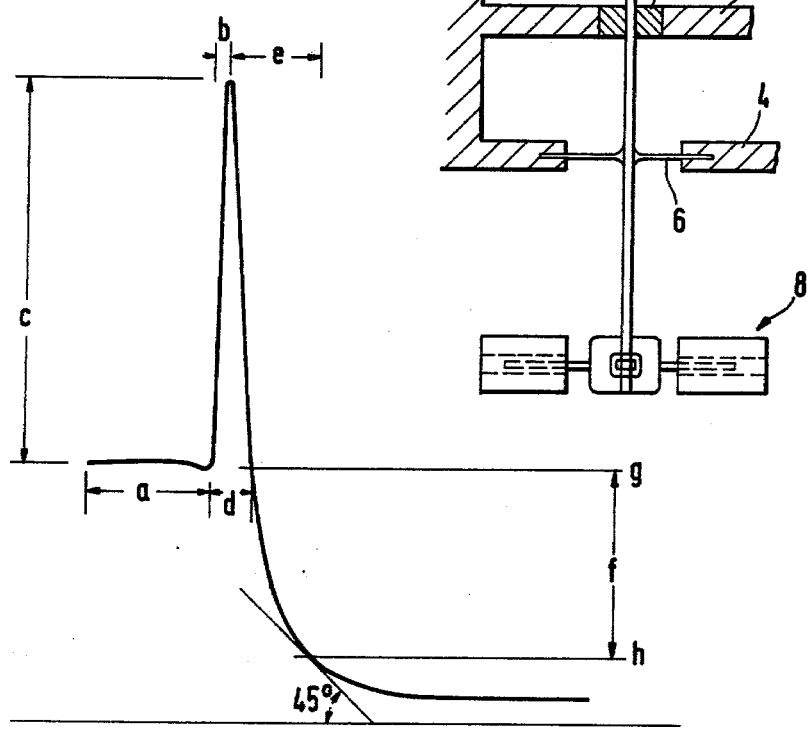
FIG. 2 is a graphic representation of the measurements made with the apparatus in FIG. 1.

The curve which is shown in FIG. 2 and which is plotted by, for example, a curve tracer of this type, clearly shows the maximum indicating the state of change. It is caused by the fact that the resilient fibrin produced in the annular gap increases the natural frequency of the orbital movement of the rod and thus shifts the orbital movement of the rod into the range of the forced frequency. The resonance occurring thereby causes the increase in amplitude, i.e. the maximum of the curve. This is exceeded and leads to the reversal of the curve as soon as the resilient moment of the coagulum increases the natural frequency of the apparatus beyond the forced frequency. Thus, very slight changes in the state of the coagulum produced, in which, for example, the blood-platelets are also involved, are manifested in a pronounced manner by the characteristic and shape of the measured curve.

The measurement curve ("resonance thrombograph") shows the following features which are given as measured variables in minutes and seconds in the horizontal and in mm in the perpendicular:

(a) = coagulation time
(b) = curve rise time
(c) = maximum amplitude
(d) = short curve descent time
(e) = long curve descent time
(f) = negative amplitude
(g) = base line ("starting deflection")
(h) = zero line (zero amplitude)

Measurement of the values of a, c and d or e is sufficient for the routine assessment of the measurement curve.

I claim:

1. Method of measuring the changes of state in solidifying fluids particularly the changes occurring in the coagulation of blood, comprising the steps of mounting a measuring vessel containing an annular space on the upper end of an upright support in a measuring system, introducing a fluid into the annular space in the measuring vessel, impressing an excitation frequency on the support and providing the support with a forced oscillatory orbital movement in the resonance range of and different from the natural frequency of the measuring system, and measuring the amplitude of the support for determining the change in state of the solidifying fluid.

2. Method, as set forth in claim 1, including the step of selecting the excitation frequency higher than the natural frequency of the support where the fluid being measured is blood.

3. Method, as set forth in claim 2, wherein the natural frequency of the support is in the range of 17 and 70 Hz.

4. Method, as set forth in claim 2, wherein the natural frequency is 35 Hz.

5. Apparatus for measuring change of state in solidifying fluids, comprising an upwardly extending frame, a beaker, an oscillatory driven means for mounting said beaker, and a member inserted into said beaker, wherein the improvement comprises that said oscillatory driven means includes an upright elastic support, said beaker mounted on the upper end of said elastic support, a resilient element for supporting said elastic support, said resilient element spaced below said beaker and extending transversely of and laterally surrounding said elastic support, a coil arrangement laterally surrounding said elastic support and spaced from said beaker and resilient element for providing circular oscillatory movement to said elastic support different from the natural frequency of said elastic support so that an orbital movement of said elastic support is produced, means for measuring the oscillatory amplitude of said elastic support, and said member being rigidly supported on said frame and extending downwardly from said frame into said beaker and forming with said beaker an annular space for receiving the fluid to be measured.

6. Apparatus, as set forth in claim 5, wherein said elastic support comprises a vertically extending resilient rod-like member.

7. Apparatus, as set forth in claim 5, wherein said coil arrangement comprises a coil generating an electromagnetic alternating field.

8. Apparatus, as set forth in claim 7, wherein the electromagnetic alternating field of said coil arrangement revolves in the circumferential direction of said rod-like member.

9. Apparatus, as set forth in claim 5, wherein said means for measuring the oscillatory amplitude comprises an oscillation sensor arranged for measuring the amplitude of the orbital movement of said elastic support without contact with said elastic support.

10. Apparatus, as set forth in claim 9, wherein said oscillation sensor is a rigidly mounted electromagnetic coil, and a movable core attached to and extending radially from said elastic support into said coil for measuring the amplitude of said elastic support.

11. Apparatus, as set forth in claim 10, including an indicating instrument connected to said electromagnetic coil for providing a trace of the change in amplitude of said elastic support.

* * * * *